(12) United States Patent
Hagiwara

(10) Patent No.: US 7,190,758 B2
(45) Date of Patent: Mar. 13, 2007

(54) X-RAY CT SYSTEM

(75) Inventor: Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 87 days.

(21) Appl. No.: 10/892,426

(22) Filed: Jul. 15, 2004

(65) Prior Publication Data
US 2005/0025278 A1 Feb. 3, 2005

(30) Foreign Application Priority Data
Jul. 29, 2003 (JP) ............... 2003-203226

(51) Int. Cl.
G01N 23/083 (2006.01)
(52) U.S. Cl. .................. 378/7; 378/98.4; 378/98.12
(58) Field of Classification Search .................. 378/7, 378/98.4, 98.12
See application file for complete search history.

(56) References Cited

U.S. PATENT DOCUMENTS

| | | | | |
|---|---|---|---|---|
| 4,029,963 | A * | 6/1977 | Alvarez et al. ............... | 378/5 |
| 4,352,986 | A * | 10/1982 | Pfeiler ......................... | 378/14 |
| 4,445,226 | A * | 4/1984 | Brody .......................... | 378/98.9 |
| 4,995,107 | A | 2/1991 | Klingenbeck | |
| 5,615,279 | A * | 3/1997 | Yoshioka et al. ............ | 382/131 |
| 5,812,629 | A * | 9/1998 | Clauser ........................ | 378/62 |
| 6,061,421 | A | 5/2000 | Hagiwara | |
| 6,173,033 | B1 | 1/2001 | Klingenbeck-Regn | |
| 6,175,609 | B1 | 1/2001 | Edic et al. | |
| 6,256,367 | B1 | 7/2001 | Vartanian | |
| 6,320,929 | B1 * | 11/2001 | Von Der Haar ............... | 378/4 |
| 6,408,049 | B1 | 6/2002 | Edic et al. | |
| 6,445,764 | B2 * | 9/2002 | Gohno et al. ................. | 378/19 |
| 6,639,964 | B2 * | 10/2003 | Schneider et al. ........... | 378/7 |
| 6,687,326 | B1 * | 2/2004 | Bechwati et al. ............ | 378/7 |
| 6,789,943 | B2 * | 9/2004 | Zapalac ....................... | 378/207 |
| 6,950,492 | B2 * | 9/2005 | Besson ......................... | 378/5 |

FOREIGN PATENT DOCUMENTS

EP 1216662 A2 12/2001

(Continued)

OTHER PUBLICATIONS

European Search Report, European Patent Application No. 04 254 542.6-2305-, 3 pgs.

(Continued)

*Primary Examiner*—Edward J. Glick
*Assistant Examiner*—Thomas R. Artman
(74) *Attorney, Agent, or Firm*—Carl B. Horton, Esq.; Armstrong Teasdale LLP

(57) ABSTRACT

A method for performing scattered radiation correction. The position of a collimator and the width of a slit are adjusted so that direct radiation will fall on one of a plurality of arrays of detectors. A predetermined phantom is scanned. The scan is performed relative to each of the plurality of arrays of detectors. Based on data detected during each scan, scattered radiation correction data is produced. The produced scattered radiation correction data is used to correct projection data acquired by scanning a subject.

10 Claims, 6 Drawing Sheets

FOREIGN PATENT DOCUMENTS

| | | |
|---|---|---|
| JP | 11-028203 | 2/1999 |
| JP | 2000-070254 | 3/2000 |
| JP | 2000-197628 | 7/2000 |
| WO | WO 01/47419 A1 | 7/2001 |
| JP | 07-213517 | 8/1995 |
| JP | 10-146334 | 6/1998 |
| JP | 2000-197628 A | 1/1999 |

OTHER PUBLICATIONS

An English translation of JP 2000-070254.
An English translation of JP 2000-197628.
An English translation of JP 11-028203.
An English translation of JP 07-213517.
An English translation of JP 10-146334.

* cited by examiner

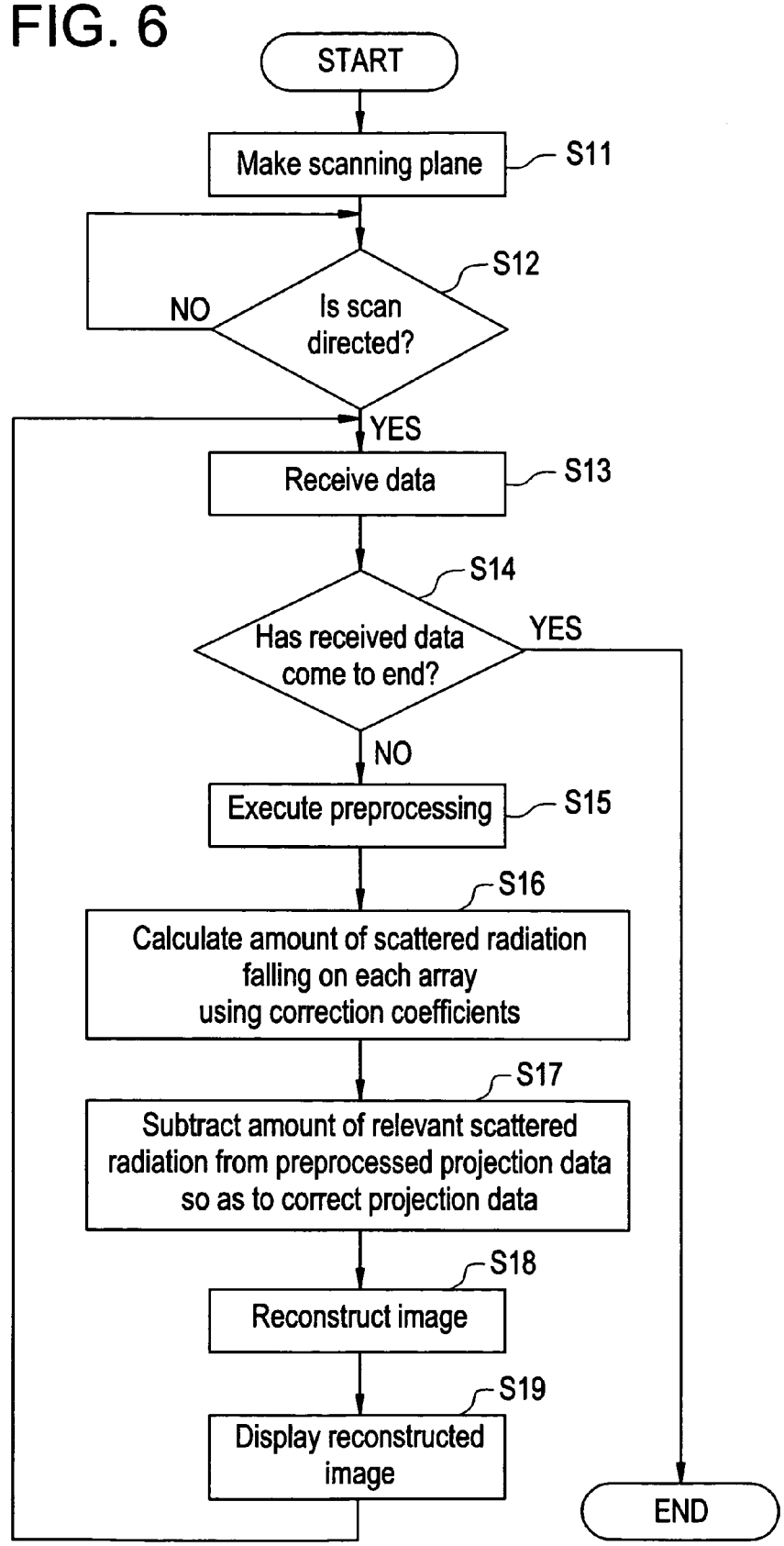

X-RAY CT SYSTEM

CROSS REFERENCE TO RELATED APPLICATIONS

This application claims the benefit of Japanese Application No. 2003-203226 filed Jul. 29, 2003.

BACKGROUND OF THE INVENTION

The present invention relates to a scattered radiation correcting technology to be implemented in an X-ray computed tomography (CT) system that produces an X-ray tomographic image of a subject through X-irradiation.

The major object of X-ray CT systems is to acquire projection data provided by X-rays having passed through a subject, and to reconstruct an X-ray tomographic image from the projection data. More particularly, first, a subject is asked to lie down on a patient couch, and transported to a bore of a gantry. A rotary assembly of the gantry in which an X-ray detecting mechanism including an X-ray tube and X-ray detectors is incorporated as an integral part thereof is driven to rotate. X-rays are irradiated to the subject from different angles, and X-rays irradiated at the respective angles and transmitted by the subject are detected. An operator console receives the detected data (projection data) and reconstructs an X-ray tomographic image by performing arithmetic operations. The sequence of steps for detecting X-rays is generally referred to as a scan.

Moreover, a so-called multi-slice X-ray CT system is known as a system having a plurality of arrays of detectors arranged in the direction of transportation in which the patient couch is transported. The multi-slice X-ray CT system has the merit that projection data representing a plurality of sections can be acquired by performing one scan. On the other hand, when the number of arrays of detectors increases, the adverse effect of scattered radiation oriented in the direction of the arrays of detectors cannot be ignored. For example, when the number of detector arrays is one or two, the majority of scattered radiation is radiated in directions in which no detector is present. It is therefore unnecessary to take account of the adverse effect of scattered radiation oriented in the direction of the detector arrays. However, when the number of detector arrays increases (for example, 32 or more), the scattered radiation oriented in the direction of the detector arrays falls on the detectors. Moreover, the amount of scattered radiation falling on each detector array is not even but markedly different especially between the edge-side detector array and the central detector array.

Incidentally, measures have been taken to cope with scattered radiation oriented in the direction of channels assigned to detectors in the past. For example, a collimator or a grid is disposed on the border of adjoining channels in order to prevent incidence of scattered radiation. However, this method brings about a decrease in an effective area of an X-ray detection surface. Moreover, an issue of an angle at which an X-ray tube is looked up cannot be ignored, and the use efficiency of X-rays is degraded. Moreover, an increase in the cost of hardware cannot be avoided because the collimator must be disposed highly precisely.

Consequently, scattered radiation oriented in the direction of the detector arrays should not be coped with by modifying hardware but should be coped with using software of data correction. Technologies for compensating the adverse effect of scattered radiation oriented in the direction of the detector arrays using software of data correction include, for example, the one described in Patent Document 1 presented later. Patent Document 1 discloses an X-ray computed tomography system that acquires scattered radiation data from output data of arrays of X-ray elements which are included in a multi-slice X-ray detector having, for example, eight arrays of X-ray elements and to which X-rays are not directly irradiated.

[Patent Document 1]
Japanese Unexamined Patent Application Publication No. 2000-197628

However, correction of scattered radiation to be performed in the X-ray computed tomography system disclosed in Patent Document 1 is not devised in consideration of the situation that an amount of scattered radiation entering each detector array is not even. Therefore, there is the room for realization of highly precise correction of scattered radiation.

SUMMARY OF THE INVENTION

Therefore, an object of the present invention is to provide an X-ray CT system capable of correcting scattered radiation more highly precisely.

According to one aspect of the present invention, thee is provided an X-ray CT system comprising: an X-ray generation source; and an X-ray detection unit having a plurality of arrays of detectors arranged in the direction of the arrays that is the direction of transportation in which a patient couch used to carry a subject is transported. The X-ray CT system further comprises: a collimator that forms a slit which limits a range of X-irradiation from the X-ray generation source; an adjusting means for adjusting the position in the direction of transportation of the collimator and the width in the direction of transportation of the slit; a scan control means for performing a scan after the adjusting means adjusts the position in the direction of transportation of the collimator and the width in the direction of transportation of the slit so that direct radiation will fall on only one of the plurality of arrays of detectors, and for performing the scan relative to each of the plurality of arrays of detectors; a correction data producing means for producing scattered radiation correction data using data detected by the X-ray detection unit during each scan performed by the scan control means; a correcting means for correcting projection data, which is acquired by scanning the subject, using the produced scattered radiation correction data; and a reconstructing means for reconstructing a tomographic image of the subject on the basis of the projection data corrected by the correcting means.

According to the present invention, there is provided an X-ray CT system capable of performing scattered radiation correction more highly precisely.

Further objects and advantages of the present invention will be apparent from the following description of the preferred embodiments of the invention as illustrated in the accompanying drawings.

BRIEF DESCRIPTION OF THE DRAWINGS

FIG. 6 is a flowchart describing an example of a series of steps that includes the step of scattered radiation correction which is a constituent feature of the embodiment and that is executed in an operator console.

DETAILED DESCRIPTION OF THE INVENTION

Referring to drawings, an embodiment will be described below.

Figure 1:
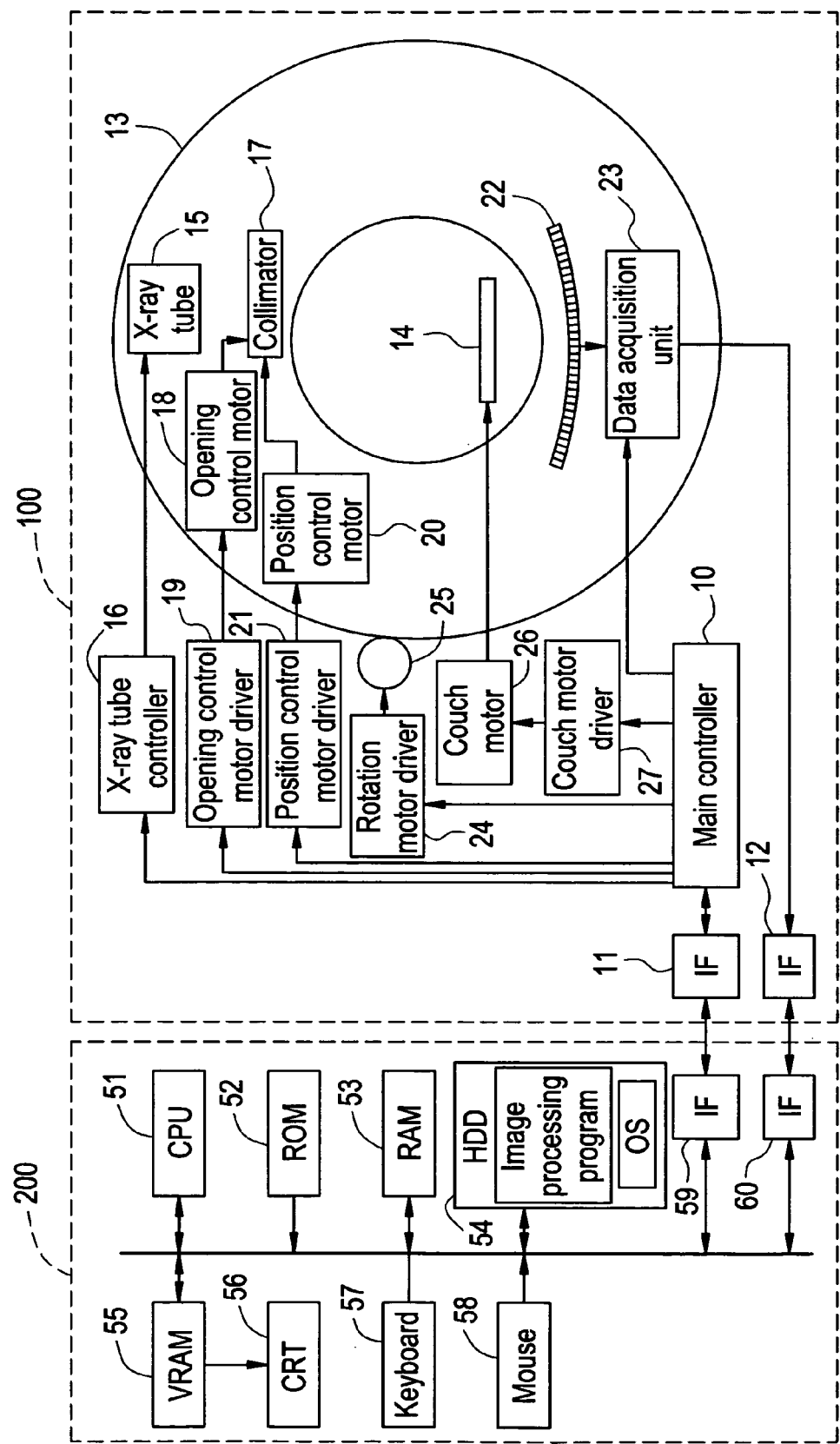
FIG. 1 shows the configuration of an X-ray CT system in accordance with an embodiment.

FIG. 1 shows the configuration of an X-ray CT system in accordance with an embodiment.

As illustrated, the present system comprises: a gantry 100 that irradiates X-rays to a subject (patient) and detects X-rays transmitted by the subject; and an operator console 200 that is used to designate various actions to be performed in the gantry 100 and that reconstructs and displays a tomographic image on the basis of data sent from the gantry 100.

The gantry 100 has a main controller 10 that is responsible for control of the entire gantry and other components described below.

Reference numerals 11 and 12 denote interfaces via which the gantry 100 communicates with the operator console 200. Reference numeral 13 denotes a rotary assembly that has a bore through which a subject lying down on a patient couch 14 is transported in a direction perpendicular to the drawing (in general, a direction corresponding to the direction of a patient's body axis, hereinafter, a z-axis direction). An X-ray tube 15 that is an X-ray generation source, a collimator 17 having an opening which limits a range of X-irradiation, an opening control motor 18 for adjusting the width in the z-axis direction of the opening of the collimator 17, and a position control motor 20 for adjusting the position in the z-axis direction of the collimator 17 are incorporated in the rotary assembly 13. The X-ray tube 15, opening control motor 18, and position control motor 20 are driven or controlled by an X-ray tube controller 16, an opening control motor driver 19, and a position control motor driver 21 respectively.

Moreover, the rotary assembly 13 includes: an X-ray detection unit 22 including a plurality of detection channels (for example, 1000 detection channels) on which X-rays radiated from the X-ray tube 15 through the collimator 17 and bore are detected; and a data acquisition unit 23 that acquires the outputs of the detection channels of the X-ray detection unit 22 as projection data. The X-ray tube 15 and collimator 17 are opposed to the X-ray detection unit 22 with the bore between them, that is, with the subject between them. The rotary assembly 13 is designed to rotate about the bore while maintaining the positional relationship among the X-ray tube 15, collimator 17, and X-ray detection unit 22. The rotation is enabled by a rotation motor 25 that is driven in response to a driving signal sent from a rotation motor driver 24. Moreover, the patient couch 14 on which a subject lies down is transported in the z-axis direction, and driven by a couch motor 26 that is driven in response to a driving signal sent from a couch motor driver 27.

The main controller 10 analyses various commands received via the interface 11, and transmits various control signals to the X-ray tube controller 16, opening control motor driver 19, position control motor driver 20, rotation motor driver 24, couch motor driver 27, and data acquisition unit 23 respectively on the basis of the results of the analysis.

Moreover, data acquired by the data acquisition unit 23 is transmitted to the operator console 200 via the interface 12.

On the other hand, the operator console 200 acts as a so-called workstation, and comprises, as illustrated, a CPU 51 that is responsive for control of the entire system, a ROM 52 in which a boot loader and other programs are stored, a RAM 53 that works as a main memory, and other components described below.

In addition to an OS, an image processing program according to which various directives are given to the gantry 100 or reconstruction and display of a tomographic image based on data received from the gantry 100 is executed is stored in a hard disk drive (HDD) 54. Moreover, a VRAM 55 is a memory in which image data according to which an image is displayed is developed. When image data or the like is developed in the VRAM 55, an image is displayed on a CRT 56. Reference numerals 57 and 58 denote a keyboard and a mouse respectively for use in determining various settings. Reference numerals 59 and 60 denote interfaces via which the operator console 200 communicates with the gantry 100 and which are connected to the interfaces 11 and 12 of the gantry 100.

The configuration of the X-ray CT system in accordance with the present embodiment has been outlined above. Next, the structures of the X-ray tube 15, collimator 17, and X-ray detection unit 22 will be detailed in conjunction with FIG. 2.

Figure 2:
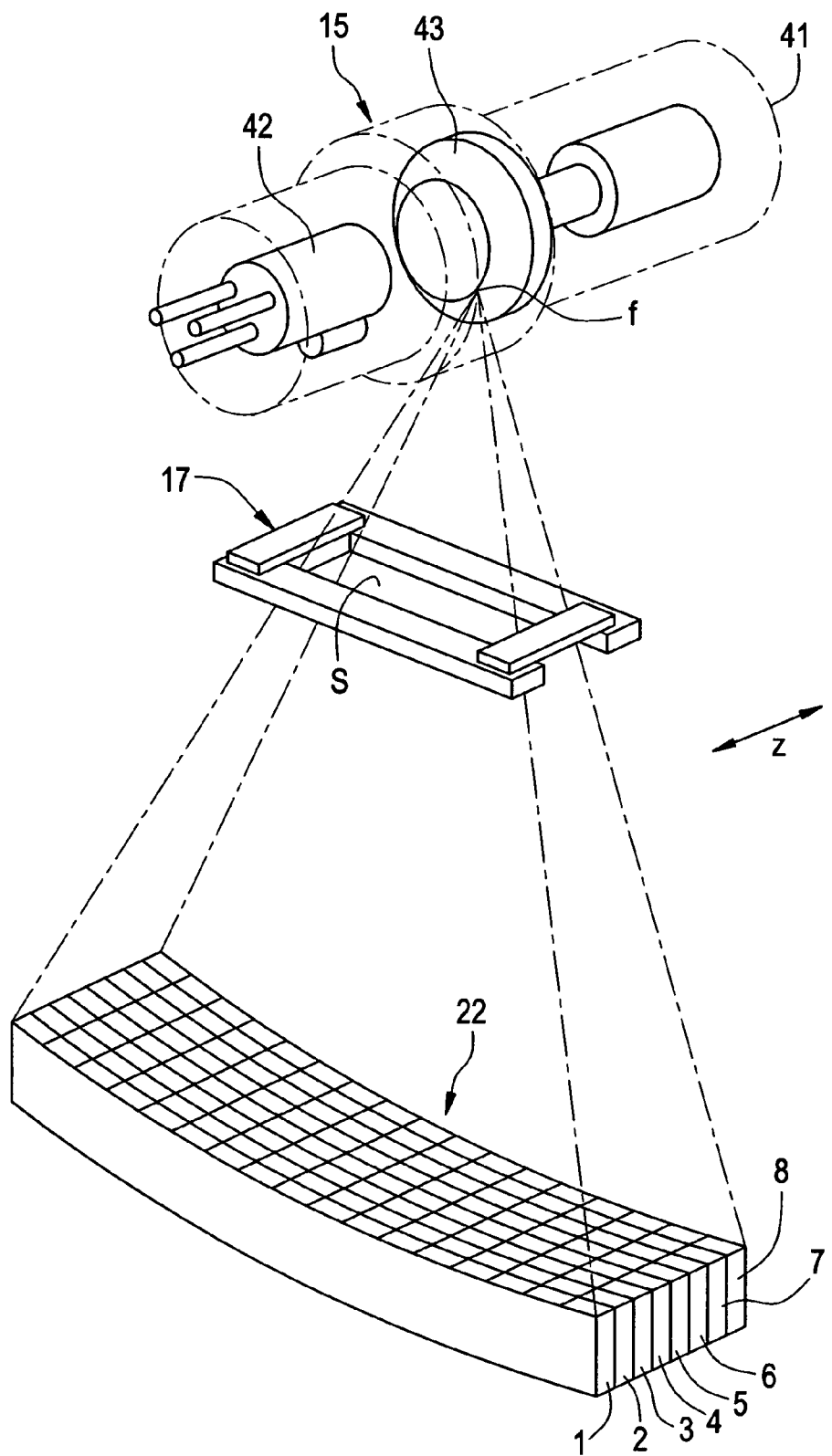
FIG. 2 shows the major portions of an X-ray tube, a collimator, and an X-ray detection unit respectively included in the present embodiment.

FIG. 2 shows the major portions of the X-ray tube 15, collimator 17, and X-ray detection unit 22 respectively. These components maintain the illustrated positional relationship while being borne by the predetermined base of the rotary assembly 13.

Referring to FIG. 2, the X-ray tube 15 is structured to have a cathode sleeve 42, in which a focusing electrode and a filament are incorporated, and a rotating target 43 accommodated in a housing 41. The X-ray tube 15 radiates X-rays from a focal point f. X-rays radiated from the X-ray tube 15 pass through a slit S formed by the collimator 17, whereby a fan-shaped beam having a predetermined angle of X-irradiation (fan angle) is formed. The X-ray detection unit 22 is structured to have, for example, eight arrays of detectors, each of which has (for example, 1000) detection channels assigned thereto over a length dependent on the fan angle, arranged in the z-axis direction (corresponding to the direction of transportation in which the patient couch 14 is transported). Herein, numbers 1, 2, 3, etc., and 8 are assigned to the detector arrays in that order with 1 assigned to the edge-side detector array. Consequently, so-called eight-array multi-slice X-ray CT is realized. The X-ray detection unit including the eight arrays of detectors is presented as a mere example. The present invention can be adapted to a system including at least two arrays of detectors.

Owing to the foregoing components, the width in the z-axis direction of the slit S which is formed by the collimator 17 (hereinafter, simply, an opening width), and the position in the z-axis direction of the collimator 17 can be adjusted by mechanically moving the collimator 17.

To begin with, an example of a mechanism for adjusting the opening width of the collimator 17 will be described below.

Figure 3:
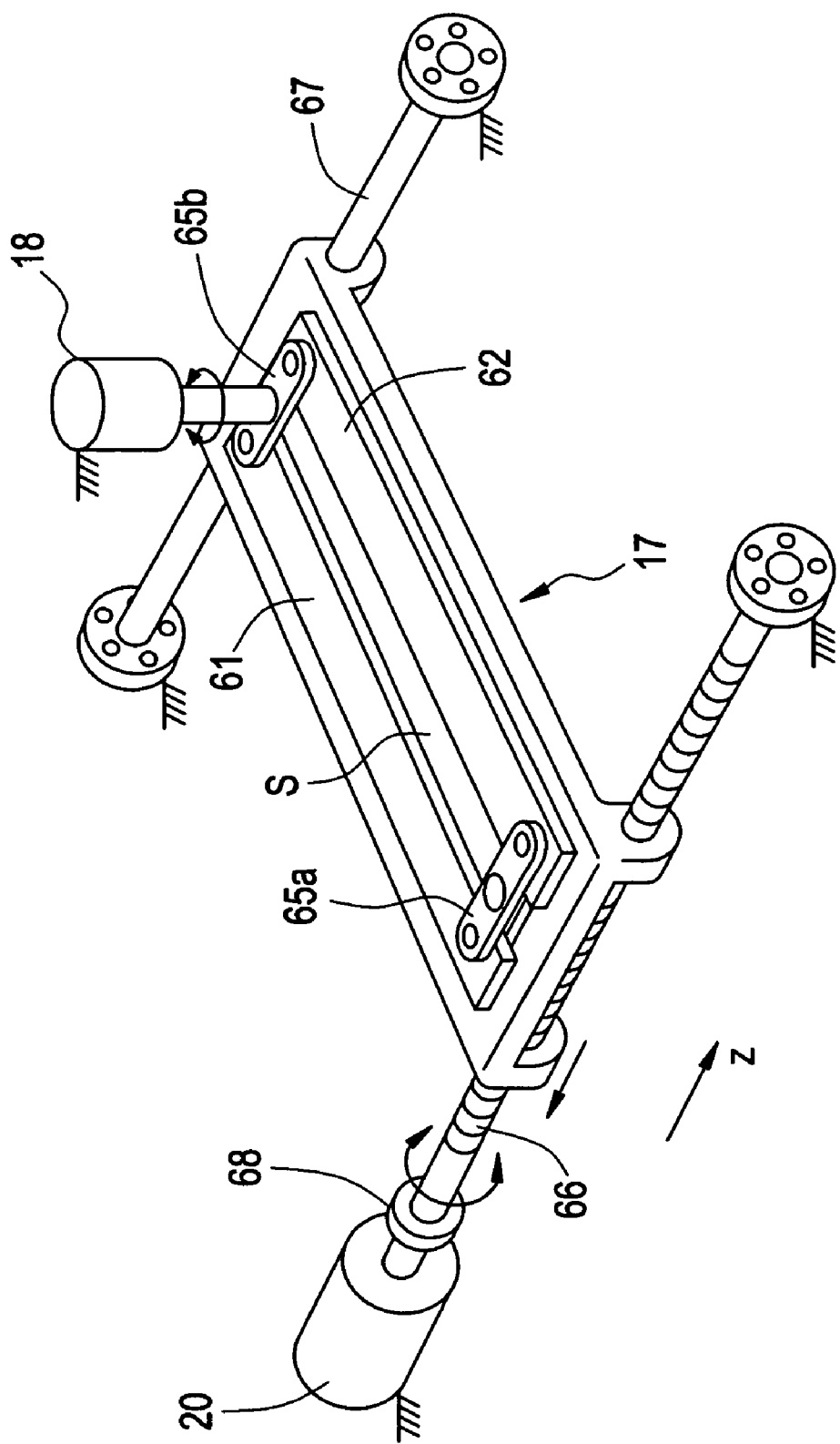
FIG. 3 shows a collimator adjusting mechanism employed in the embodiment.

FIG. 3 shows the mechanism for adjusting the collimator 17 employed in the present embodiment. Incidentally, hatching in FIG. 3 indicates that the collimator 17 is secured to the predetermined base of the gantry 13.

Shielding plates 61 and 62 of the collimator 17 have the ends thereof linked by link members 65a and 65b respectively so that they can be turned freely, whereby a parallel movement linking mechanism is constructed. Consequently, the shielding plates 61 and 62 can hold each other in parallel. A gap between the two shielding plates 61 and 62 serves as the slit S through which X-rays are passed. Moreover, a rotation shaft is fixed to the center of each of the link members 65a and 65b. An output shaft of the opening width control motor 18 is fixed to the rotation shaft of the link member 65b.

Owing to the foregoing structure, when the opening width control motor 18 is driven in order to rotate the rotation shaft, the shielding plates 61 and 62 are turned to gradually widen or narrow the gap while remaining parallel to each other. Consequently, the opening width of the slit S can be controlled.

Moreover, the collimator 17 is supported by a ball screw 66, which is disposed in the z-axis direction and fixed to one end of the collimator 17, and a linear guide 67 that is disposed in the z-axis direction and fixed to the other end of the collimator 17. The ball screw 66 is attached to the output shaft of the position control motor 20 with a coupling 68 between them. The rotating motion of the ball screw 66 made when the ball screw is driven by the position control motor 20 is converted into the linear motion in the z-axis direction of the collimator 17, whereby the position of the entire collimator 17 can be adjusted.

However, the foregoing adjusting mechanism is presented as a mere example. The present invention is not limited to the adjusting mechanism. Any other structure may be adopted for the adjusting mechanism.

In the X-ray CT system having the foregoing components, projection data is acquired as mentioned below.

To begin with, the position in the z-axis direction of the rotary assembly 13 is fixed with a subject positioned in the bore of the rotary assembly 13. An X-ray beam is then irradiated from the X-ray tube 15 to the subject (projection of X-rays), and the transmitted X-rays are detected by the X-ray detection unit 22. Detection of the transmitted X-rays is performed in a plurality N of directions of views. (for example, N=1000) by rotating the X-ray tube 15 and X-ray detection unit 22 about the subject (that is, by changing a projection angle (or view angle)), for example, 360°.

The detected transmitted X-rays are converted into digital data by the data acquisition unit 23, and transferred to the operator console 200 via the interface 12. The sequence of steps is referred to as a scan that is one unit. The position of a scan is sequentially shifted in the z-axis direction by a predetermined length, and the next scan is performed. This scanning technique is referred to as an axial scanning technique. Alternatively, a helical scanning technique of acquiring projection data by continuously moving the patient couch 14 along with the rotation of the gantry 13 (the X-ray tube 15 and X-ray detector 22 helically revolve about a subject) will do.

In the operator console 200, the projection data sent from the gantry 100 is stored in the HDD 54. Moreover, for example, predetermined reconstruction and convolution are performed, and back projection is performed in order to reconstruct a tomographic image. Herein, the operator console 200 reconstructs a tomographic image in real time using projection data sequentially sent from the gantry 100 during a scan. Thus, an up-to-date tomographic image is always displayed on the CRT 56. Furthermore, projection data may be retrieved from the HDD 54 in order to reconstruct an image.

Scattered radiation correction that is a constituent feature of the present embodiment will be described below.

As described previously, an amount of scattered radiation falling on each detector array is presumably not constant because of a difference in the shape in the direction of detector arrays of a subject or a difference in the structure of an intracorporeal tissue of a subject. According to the present embodiment, therefore, an amount of scattered radiation falling on each detector array is measured using a predetermined phantom. Scattered radiation correction data is produced based on the results of the measurement (scattered radiation correction data acquisition). Projection data acquired by actually scanning a subject is corrected based on the scattered radiation correction data.

Figure 4:
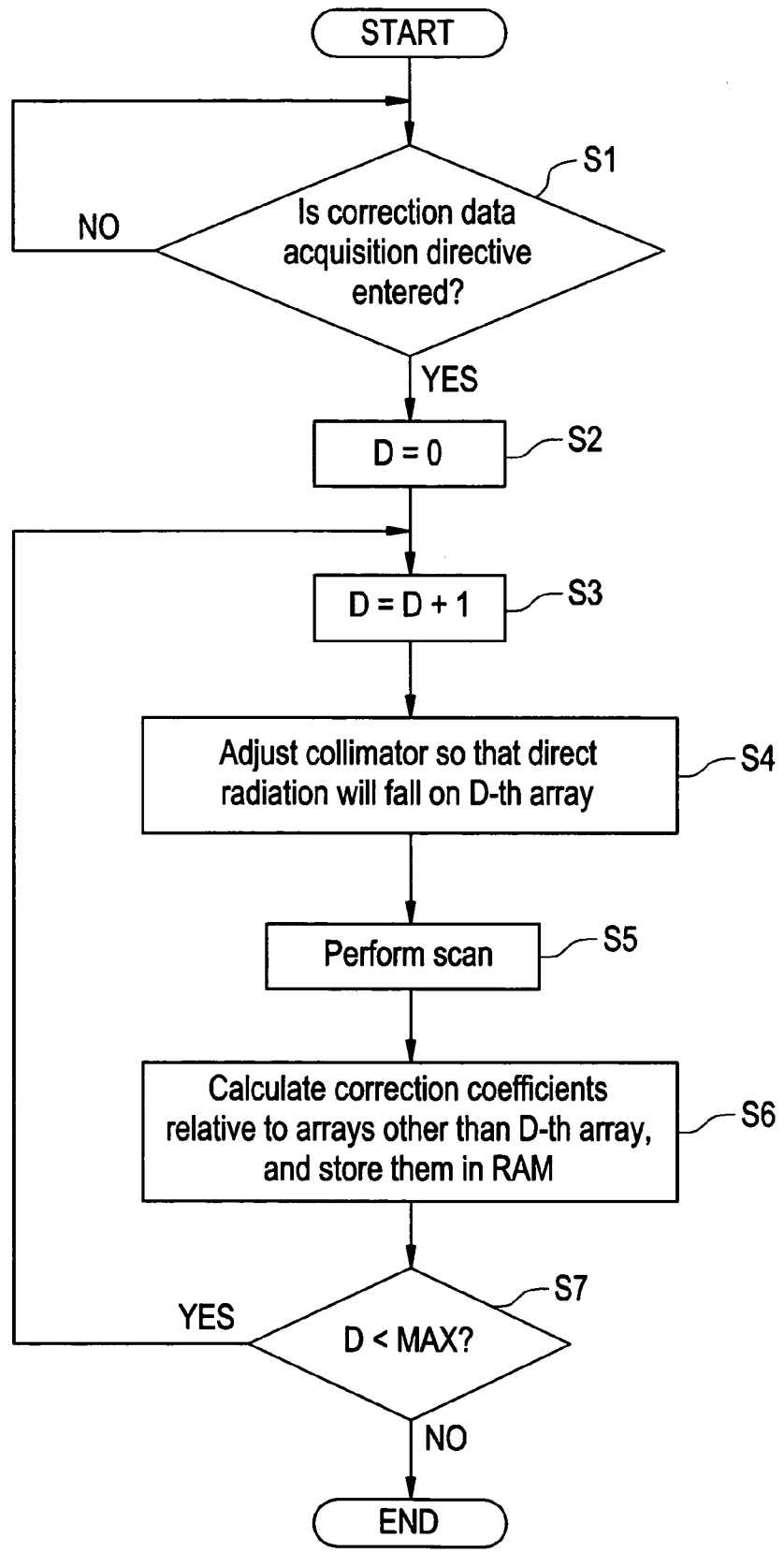
FIG. 4 is a flowchart describing an example of scattered radiation correction data acquisition that is a constituent feature of the embodiment.

FIG. 4 is a flowchart describing an example of scattered radiation correction data acquisition employed in the present embodiment.

Before scattered radiation correction data acquisition is started, a predetermined phantom is placed on the patient couch 14 in advance. For example, an acrylic container filled with water and having a nearly elliptic section in a direction orthogonal to the direction of transportation in which the patient couch 14 is transported is used as the phantom.

First, at step S1, it is waited until a correction data acquisition directive is entered at the keyboard 57 or mouse 58 included in the operator console 200. As soon as the correction data acquisition directive is confirmed, control is passed to step S2. At step S2, a variable D representing a detector array number is initialized to 0. At step S3, the D value is incremented by one.

Thereafter, the position in the z-axis direction of the collimator 17 and the width of the slit are adjusted so that direct radiation of X-rays will fall on the D-th array alone (step S4). In this state, a scan is performed (step S5). In the present specification, the term "direct radiation" signifies X-rays linearly falling on the X-ray detectors from the X-ray generation source, and is used as the antonym of scattered radiation.

Figure 5:
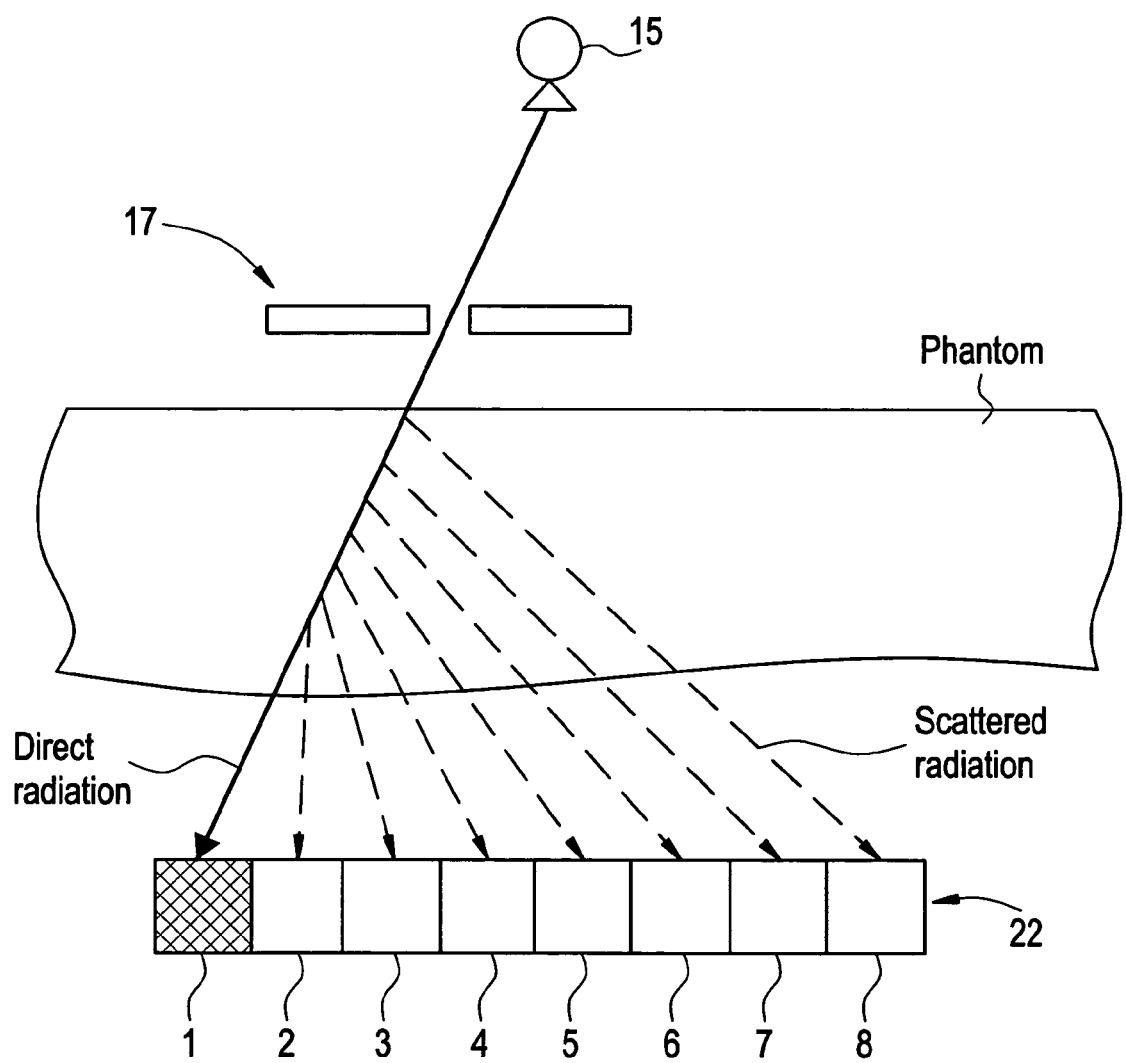
FIG. 5 shows a pattern expressing scattered radiation that falls on detector arrays.

FIG. 5 shows a pattern expressing the state of the collimator adjusted at step S4 with the D value set to 1, wherein direct radiation falls on the first detector array alone. At the same time, X-rays irregularly reflected from the substance of the phantom fall as scattered radiation on the other second to eighth detector arrays.

Thereafter, at step S6, a correction coefficient is calculated as scattered radiation correction data. The correction coefficient is calculated relative to each detection channel of each of the detector arrays other than the detector array on which direct radiation falls. At step S5, direct radiation falls on the D-th detector array alone, and a scan is performed in order to acquire the i-th view. Herein, assume that projection data contained in the i-th view and detected by a detector that is included in the d-th array (where d is not equal to D) and that is assigned the j-th channel is called projection data p(d,i,j). In this case, a correction coefficient $\alpha_D(d,i,j)$ calculated from the i-th view relative to the detector that is included in the d-th array and that is assigned the j-th channel is expressed as follows:

$$\alpha_D(d,i,j) = p(d,i,j)/p(D,i,j) \tag{1}$$

The correction coefficient understandably represents the ratio of the intensity of scattered radiation to the intensity of direct radiation. Hereinafter, since the correction coefficient is apparently calculated relative to each channel, the projection data p(d,i,j) and correction coefficient $\alpha_D(d,i,j)$ shall be represented by projection data p(d,i) and a correction coefficient $\alpha_D$ (d,i) with the channel variable i omitted. Consequently, the expression (1) is rewritten as follows:

$$\alpha_D(d,i)=p(d,i)/p(D,i) \quad (2)$$

The thus calculated correction coefficient $\alpha_D$ (d,i) is stored in, for example, the RAM 53.

At step S7, it is verified whether the D value is smaller than the total number of detector arrays, MAX (MAX=8 in the present embodiment), included in the X-ray detection unit 22. If D<MAX is met, control is returned to step S3, and processing is repeated relative to the next detector array. When the processing has been performed relative to all the detector arrays, D<MAX is not met any longer. The process is then terminated.

Consequently, a correction coefficient is calculated as scattered radiation correction data relative to each detector array using a phantom.

FIG. 6 is a flowchart describing an example of a series of steps including the step of scattered radiation correction, which is a constituent feature of the present embodiment, and being executed in the operator console 200. A program having the same contents as the flowchart is contained in the image processing program stored in the hard disk drive 54 included in the operator console 200. After the power supply is turned on, the program is loaded in the RAM 53 and run by the CPU 51.

First, at step S11, a scanning plan is made. For example, such scanning conditions as a slice thickness, scan start and end positions, a current that flows into the X-ray tube 15, and a rotating speed of the gantry rotary assembly 13 are determined through a graphic user interface (GUI) provided by the image processing program. The scanning plan itself is already known, and the details thereof will therefore be omitted. The determined scanning conditions are stored in the RAM 53.

At the next step S12, it is judged from an entry made at the keyboard 57 or mouse 58 whether a scan start directive is entered. If the scan start directive is entered, a scan start command specifying the scanning conditions, which are determined at step S11, as parameters is transmitted to the gantry 100. This causes the gantry 100 to scan a subject. Assume that each scan is performed for a slice thickness allowing X-rays to fall directly on all the detector arrays.

At step S13, data acquired during the scan is received from the gantry 100. At step S14, it is monitored whether all data items have been received.

At step S15, predetermined preprocessing including reference correction, beam hardening, and correction of the physical characteristics of X-ray detectors is performed. The preprocessing is selectively performed if necessary and bears no direct relation to the present invention. The details of the preprocessing will therefore be omitted.

At step S16, a correction coefficient calculated during the scattered radiation correction data acquisition is used to calculate an amount of scattered radiation, scatD, falling on a detector array D during acquisition of each view. Specifically, amounts of scattered radiation, $scat_1(i)$ to $scat_8(i)$, falling on the first to eighth respective detector arrays during acquisition of the i-th view are expressed as presented below. Herein, $\alpha_D$ (d,i) denotes a correction coefficient that is calculated from the i-th view relative to each of the detectors belonging to the d-th array under the condition that direct radiation should enter the D-th detector array alone. Moreover, p(d,i) denotes the projection data contained in the preprocessed i-th view and detected by each of the detectors belonging to the d-th array.

$$scat_1(i)=\alpha_2(1,i)p(2,i)+\alpha_3(1,i)p(3,i)+\alpha_4(1,i)p(4,i)+\alpha_5(1,i)p(5,i)+\alpha_6(1,i)p(6,i)+\alpha_7(1,i)p(7,i)+\alpha_8(1,i)p(8,i)$$

$$scat_2(i)=\alpha_1(2,i)p(1,i)+\alpha_3(2,i)p(3,i)+\alpha_4(2,i)p(4,i)+\alpha_5(2,i)p(5,i)+\alpha_6(2,i)p(6,i)+\alpha_7(2,i)p(7,i)+\alpha_8(2,i)p(8,i)$$

$$scat_3(i)=\alpha_1(3,i)p(1,i)+\alpha_2(3,i)p(2,i)+\alpha_4(3,i)p(4,i)+\alpha_5(3,i)p(5,i)+\alpha_6(3,i)p(6,i)+\alpha_7(3,i)p(7,i)+\alpha_8(3,i)p(8,i)$$

$$scat_4(i)=\alpha_1(4,i)p(1,i)+\alpha_2(4,i)p(2,i)+\alpha_3(4,i)p(3,i)+\alpha_5(4,i)p(5,i)+\alpha_6(4,i)p(6,i)+\alpha_7(4,i)p(7,i)+\alpha_8(4,i)p(8,i)$$

$$scat_5(i)=\alpha_1(5,i)p(1,i)+\alpha_2(5,i)p(2,i)+\alpha_3(5,i)p(3,i)+\alpha_4(5,i)p(4,i)+\alpha_6(5,i)p(6,i)+\alpha_7(5,i)p(7,i)+\alpha_8(5,i)p(8,i)$$

$$scat_6(i)=\alpha_1(6,i)p(1,i)+\alpha_2(6,i)p(2,i)+\alpha_3(6,i)p(3,i)+\alpha_4(6,i)p(4,i)+\alpha_8(6,i)p(5,i)+\alpha_7(6,i)p(7,i)+\alpha_8(6,i)p(8,i)$$

$$scat_7(i)=\alpha_1(7,i)p(1,i)+\alpha_2(7,i)p(2,i)+\alpha_3(7,i)p(3,i)+\alpha_4(7,i)p(4,i)+\alpha_5(7,i)p(5,i)+\alpha_6(7,i)p(6,i)+\alpha_8(7,i)p(6,i)$$

$$scat_8(i)=\alpha_1(8,i)p(1,i)+\alpha_2(8,i)p(2,i)+\alpha_3(8,i)p(3,i)+\alpha_4(8,i)p(4,i)+\alpha_5(8,i)p(5,i)+\alpha_6(8,i)p(6,i)+\alpha_7(8,i)p(7,i) \quad (3)$$

In other words, the intensity of scattered radiation falling on one detector array is calculated by weighting the intensities of X-rays falling on the other detector arrays using relevant correction coefficients, and adding up the weighted intensities. This calculation is performed on all views.

Thereafter, at step S17, the intensity of scattered radiation, scatD(i), calculated at step S16 is subtracted from the projection data p(d,i) preprocessed at step S15 in order to work out projection data p'(d,i) that has data, which is provided by scattered radiation, compensated. Specifically, projection data items that are contained in the i-th view, detected by the first to eighth respective detector arrays, and each have data, which is provided by scattered radiation, compensated are expressed as follows:

$$p'(1,i)=p(1,i)-scat_1(i)$$

$$p'(2,i)=p(2,i)-scat_2(i)$$

$$p'(3,i)=p(3,i)-scat_3(i)$$

$$p'(4,i)=p(4,i)-scat_4(i)$$

$$p'(5,i)=p(5,i)-scat_5(i)$$

$$p'(6,i)=p(6,i)-scat_6(i)$$

$$p'(7,i)=p(7,i)-scat_7(i)$$

$$p'(8,i)=p(8,i)-scat_8(i) \quad (4)$$

The above calculation is performed on all views.

At step S18, the projection data having data, which is provided by scattered radiation, compensated at step S17 is used to perform image reconstruction. An X-ray tomographic image of a subject is thus constructed, and displayed on the CRT 56 at step S19.

According to the foregoing present embodiment, a phantom is used to measure an amount of scattered radiation falling on each detector array from each view. Scattered radiation correction data is produced based on the results of the measurement. Projection data contained in each view acquired by actually scanning a subject is corrected with the scattered radiation correction data. Consequently, high-precision scattered radiation correction is realized with consideration taken into the fact that the adverse effect of scattered radiation is not even for each detector array.

Many widely different embodiments of the invention may be constructed without departing from the spirit and the scope of the present invention. It should be understood that the present invention is not limited to the specific embodiments described in the specification, except as defined in the appended claims.

The invention claimed is:

1. An X-ray CT system comprising an X-ray generation source, and an X-ray detection unit having a plurality of arrays of detectors arranged in a direction of transportation in which a patient couch used to carry a subject is transported, said X-ray CT system comprising:
    a collimator that forms a slit which limits a range of X-irradiation from said X-ray generation source;
    an adjusting device for adjusting the position in the direction of transportation of said collimator and the width in the direction of transportation of said slit;
    a scan control device for performing a scan after said adjusting device adjusts the position in the direction of transportation of said collimator and the width in the direction of transportation of said slit so that direct radiation of X-rays will fall on one of the plurality of arrays of detectors, and for performing the scan relative to each of the plurality of arrays of detectors;
    a correction data producing device for producing scattered radiation correction data on the basis of data detected by said X-ray detection unit during each scan performed by said scan control device, wherein said correction data producing device calculates a correction coefficient, which represents a ratio of an intensity of scattered radiation to an intensity of direct radiation, relative to each of the plurality of arrays of detectors using each view acquired during each scan performed by said scan control device;
    a correcting device for correcting projection data, which is acquired by scanning a subject, using the produced scattered radiation correction data, wherein said correcting device calculates, by computing a weighted sum, an intensity of scattered radiation generated during a scan of the subject; and
    a reconstructing device for reconstructing a tomographic image of the subject on the basis of the projection data corrected by said correcting device.

2. An X-ray CT system according to claim 1, further comprising a phantom, wherein said scan control device is activated to work on said phantom.

3. An X-ray CT system according to claim 2, wherein a section of said phantom in a direction orthogonal to the direction of transportation is nearly elliptic.

4. An X-ray CT system according to claim 1, wherein said correcting device uses the correction coefficient to calculate the intensity of scattered radiation falling on each detector array, and subtracts the intensity of scattered radiation from projection data acquired by scanning the subject so as to correct the projection data.

5. An X-ray CT system according to claim 4, wherein said correcting device calculates the intensity of scattered radiation falling on one detector array by weighting a plurality of intensities of X-rays falling on the other detector arrays using relevant correction coefficients, and adding up the weighted intensities of X-rays.

6. A method for compensating the adverse effect of scattered radiation on acquired projection data of a subject, which is implemented in an X-ray CT system comprising an X-ray generation source, an X-ray detection unit having a plurality of arrays of detectors arranged in a direction of transportation in which a patient couch used to carry a subject is transported, a collimator that forms a slit which limits a range of X-irradiation from said X-ray generation source, and an adjusting device for adjusting the position in the direction of transportation of said collimator and the width in the direction of transportation of said slit, said method comprising:
    a scan control step of performing a scan after said adjusting device adjusts the position in the direction of transportation of said collimator and the width in the direction of transportation of said slit so that direct radiation of X-rays will fall on one of said plurality of arrays of detectors, and of performing the scan relative to each of said plurality of arrays of detectors;
    a correction data producing step of producing scattered radiation correction data on the basis of data detected by said X-ray detection unit during each scan performed at said scan control step, wherein at said correction data producing step, a correction coefficient representing the ratio of an intensity of scattered radiation to an intensity of direct radiation is calculated relative to each of said plurality of arrays of detectors using each view acquired during each scan performed at said scan control step; and
    a correcting step of correcting projection data, which is acquired by scanning a subject, using the produced scattered radiation correction data, wherein said correcting projection data comprises calculating, by computing a weighted sum, an intensity of scattered radiation generated during a scan of the subject.

7. A method according to claim 6, wherein said scan control step is executed for a predetermined phantom.

8. A method according to claim 7, wherein a section of said phantom in a direction orthogonal to the direction of transportation is nearly elliptic.

9. A method according to claim 6, wherein at said correcting step, the correction coefficient is used to calculate the intensity of scattered radiation falling on each detector array, and the intensity of relevant scattered radiation is subtracted from projection data, which is acquired by scanning a subject, in order to correct the projection data.

10. A method according to claim 9, wherein at said correcting step, the intensity of scattered radiation falling on one detector array is calculated by weighting a plurality of intensities of X-rays falling on the other detector arrays using relevant correction coefficients, and adding up the weighted intensities of X-rays.

* * * * *